United States Patent
Chen et al.

(10) Patent No.: US 7,742,894 B2
(45) Date of Patent: Jun. 22, 2010

(54) MULTI-PERSON POSE RECOGNITION SYSTEM USING A ZIGBEE WIRELESS SENSOR NETWORK

(75) Inventors: Chun-Wei Chen, Shalu Township, Taichung County (TW); Kai-Tai Song, Hsinchu (TW)

(73) Assignee: National Chiao Tung University, Hsinchu (TW)

( * ) Notice: Subject to any disclaimer, the term of this patent is extended or adjusted under 35 U.S.C. 154(b) by 0 days.

(21) Appl. No.: 12/048,678

(22) Filed: Mar. 14, 2008

(65) Prior Publication Data

US 2009/0161915 A1    Jun. 25, 2009

(30) Foreign Application Priority Data

Dec. 24, 2007    (TW) .............................. 96149633 A (51) Int. Cl.
G01C 9/00    (2006.01)
(52) U.S. Cl. .......................... 702/150; 702/66; 702/82; 702/94; 340/669; 340/573.1
(58) Field of Classification Search ................... 702/40, 702/57, 66, 82, 94–97, 104, 142, 149–150, 702/189–191; 73/510–511; 340/669, 686.1, 340/573.1, 573.7, 699
See application file for complete search history.

(56) References Cited

U.S. PATENT DOCUMENTS

| | | | |
|---|---|---|---|
| 6,201,476 B1 | 3/2001 | Depeursinge et al. | |
| 7,210,240 B2 | 5/2007 | Townsend et al. | |
| 2003/0139692 A1* | 7/2003 | Barrey et al. | 600/595 |
| 2006/0123053 A1* | 6/2006 | Scannell, Jr. | 707/104.1 |
| 2007/0063850 A1* | 3/2007 | Devaul et al. | 340/573.1 |
| 2007/0208233 A1* | 9/2007 | Kovacs | 600/300 |
| 2008/0001735 A1* | 1/2008 | Tran | 340/539.22 |
| 2008/0133277 A1* | 6/2008 | Jang et al. | 705/3 |
| 2008/0234935 A1* | 9/2008 | Wolf et al. | 701/216 |

(Continued)

OTHER PUBLICATIONS

CSR, BlueCore(trademark)3-Multimedia, Oct. 2006, CSR, CS-101560-DSP1, pp. 1-108.*

(Continued)

*Primary Examiner*—Hal D Wachsman
*Assistant Examiner*—Mi'schita' Henson
(74) *Attorney, Agent, or Firm*—Antonelli, Terry, Stout & Kraus, LLP; Hung H. Bui, Esq.

(57) ABSTRACT

In the present invention, a multi-person pose recognition system has been developed. This system includes a body pose detection module, a CC2420DBK board and a multi-person pose monitoring software module. The body pose detection module includes a triaxial accelerometer, a Zigbee chip and an 8-bit microcontroller. Several body pose detection modules and the CC2420DBK board form a Zigbee wireless sensor network (WSN). The CC2420DBK board functions as the receiver of the Zigbee WSN and communicates with a robot onboard computer or a host computer through a RS-232 port. The multi-person pose monitoring software monitors and records activities of multiple users simultaneously. The present invention provides a pose recognition algorithm by combining time-domain analysis and wavelet transform analysis. This algorithm has been implemented in the microcontroller of a body pose estimation module. Through the algorithm, the system can recognize seven body poses: falling, standing, sitting, lying, walking, going upstairs and going downstairs.

10 Claims, 10 Drawing Sheets

U.S. PATENT DOCUMENTS

2008/0275348 A1* 11/2008 Catt et al. .................. 600/483
2009/0002217 A1*  1/2009 Kryze et al. ................ 341/176
2009/0129273 A1*  5/2009 Zou .......................... 370/235

OTHER PUBLICATIONS

A MasterThesis submitted to Department of Electrical and Control Engineering College of Electrical and Computer Engineering, National Chiao Tung University, "Multi-Person Pose Estimation Using a Zigbee Sensor Network", Chun-Wei Chen, published on Jul. 2007, 67 pages.

C. V. C. Bouten, et al., "A triaxial accelerometer and portable data processing unit for the assessment of daily physical activity, " IEEE Trans. Biomedical Engineering, vol. 44, No. 3, pp. 136-147, 1997.

S. Tanaka et al., "A new portable device for ambulatory monitoring of human posture and walking velocity using miniature accelerometers and gyroscope," in Proc. of the 26th Annual International Conference of the IEEE EMBS, San Francisco, CA, USA, Sep. 1-5, 2004, pp. 2283-2286.

D. M. Karantonis, et al., "Implementation of a Real-Time Human Movement Classifier Using a Triaxial Accelerometer for Ambulatory Monitoring," IEEE Trans. Information Technology in Biomedicine, vol. 10, No. 1, pp. 156-167, 2006.

* cited by examiner

MULTI-PERSON POSE RECOGNITION SYSTEM USING A ZIGBEE WIRELESS SENSOR NETWORK

CROSS-REFERENCE TO RELATED APPLICATION

This application claims all benefits accruing under 35 U.S.C. §119 from Taiwanese Patent Application No. 096149633, filed on Dec. 24, 2007 in the Intellectual Property Office Ministry of Economic Affairs, Republic of China, the disclosure of which is incorporated by reference herein.

FIELD OF THE INVENTION

The present invention relates to a multi-person pose recognition system, and more particularly to a multi-person pose recognition system using a ZIGBEE wireless sensor network (WSN).

BACKGROUND OF THE INVENTION

In view of the modern medical technology development, the average life of human being is prolonged and the aging population is increasing year by year. All these give rise to lots of issues concerning the home care of aging people. As the time of aging people being home alone increases, if they incurs any contingent condition (e.g. tumble or prolonged sickness), their children may not be aware of that in time and such delay usually results in regrettable outcome.

So far, the countermeasure to this problem is to mount a camera in the room of aging people or in the home for the aged so as to keep track of their activities. However, in addition to blind zones, using the camera also requires additional labor to constantly watch the video images taken thereby. Such job is not only boring but also unrespectful of privacy of the aged. Nowadays, some human pose detection systems developed by using inertial sensor have been brought into play to attain the home care effect under the premise of no breach of privacy.

As to the body pose detection system based on the inertia sensor, a prior art represented by Bouten etl al. [C. V. C. Bouten, K. T. M. Koekkoek, M. Verduin, R. Kodde and J. D. Janssen, "A triaxial accelerometer and portable data processing unit for the assessment of daily physical activity", IEEE Tans. Biomedical Engineering, vol. 44, no. 3, pp. 136-147, 1997.], develops a portable device for recording and determining user's daily activities. Bouten etl al. employ tri-axis accelerometer to measure the dynamic acceleration of human body, use the dynamic acceleration of human body to measure the energy consumed by human body, and determine pose by the energy consumption caused by different movement. Such prior art determines the movement with large energy difference by using a tri-axis accelerometer. Whereas, if determining pose completely by consumed energy, it is prone to a misjudged condition while determining movement with insignificant energy consumption difference and is unlikely to determine static pose.

Besides, another prior art represented by Tanaka etl al. [S. Tanaka, K. Motoi, M. Nogawa and K. Yamakoshi, "A new portable device for ambulatory monitoring of human posture and walking velocity using miniature accelerometers and gyroscope," in Proc. of the 26th Annual International Conference of the IEEE EMBS, San Francisco, USA, 2004, pp. 2283-2286.], discloses a simple relationship which utilizes an accelerometer to calculate the inclination angle of each portion of human body, thereby observing poses of human body. However, such system needs to be mounted to three portions of a body so that it is not convenient to wear and the sensors thereof are difficult to be bundled with normal living utensils such as belt, shoes and so forth, making it hardly practical.

Moreover, refer to the technique addressed by Karantonis etl al. [D. M. Karantonis, M. R. Narayanan, M. Mathie, N. H. Lovell and B. G. Celler, "Implementation of a Real-Time Human Movement Classifier Using a Triaxial Accelerometer for Ambulatory Monitoring," IEEE Trans. Information Technology in Biomedicine, vol. 10, Issue. 1, pp. 156-167, 2006.]. Such prior art combines the research results of various researchers, and the algorithm thereof is realized within a microcontroller. Although its system uses a Zigbee module to transmit the determination result of body pose, the system is not applied to a Zigbee network. In contrast, the present invention employs multiple Zigbee modules to construct a Zigbee wireless sensor network (WSN) (discussed in details later) so as to simultaneously observe the poses of multiple users, increase the detection range and upgrade the system's utility.

In addition to the above-mentioned description, few points concerning the drawbacks and the improvement of the prior arts are further summarized as follows:

(I) Many body pose recognition algorithms based on inertia sensor adopt time-domain or frequency-domain analysis. The poses that can be determined by those algorithms are quite limited. Hence, if the time-domain analysis and the frequency-domain analysis can be integrated, more poses may be determined.

(II) Many body pose recognition algorithms proposed by research have massive computation demand, making them infeasible for being directly loaded in a microcontroller on human body to execute the algorithms. Consequently, it is necessary for the sensed data to be stored first and then analyzed in an off-line manner. In that sense, real-time determination of pose is out of the question. To be more practical, a system equipped with real-time pose-recognizing capability must be developed. Furthermore, a body pose detection module for detecting poses of human body shall be featured by compact size and the feasibility to be integrated with daily living utensils so as to relieve user's inconvenience while carrying it.

(III) Almost all the related researches focusing on the pose detection of single target fail to determine multi-person poses at the same time. Whereas, there are usually more than one person requiring care at home. As a result, a future home care system shall develop to meet the goal of taking care of a plurality of people at the same time.

Meanwhile, because the current robotic technology is gradually mature, many researchers hope that a future robot may gradually step into a family, not only helping the works of human being but also playing a role for home security and care of the aged. Therefore, the present invention develops a set of multi-person pose recognition system attempting to be integrated with a robot through the system, such that a robot servicing at home could assist to take care the aged domestically. The body pose detection module carried by the aged uses sensors to sense a pose of the aged. Through a Zigbee WSN, a robot may simultaneously watch multiple care recipients. Thus, the system is ideal for the application to multiple care recipients in the home-for-the-aged or at home. When the robot senses an accident that a care recipient falls down, the robot could immediately go to the scene, where the accident occurs, to concern and immediately issue an alarm to inform the children of the aged, thereby further securing the home security of the aged.

The first object of the present invention is to provide a multi-person pose recognition system using a Zigbee WSN, which may recognize seven types of body poses of human namely fall down, stand, sit, lie down, go upstairs, go downstairs and walk.

The second object of the present invention is to provide a body pose detection module for realizing the pose detection algorithm, which constitutes a Zigbee WSN with a development board (CC2420DBK) of the Zigbee WSN so as to achieve the effect of observing multi-person poses.

The third object of the present invention is to provide a pose detection algorithm combining time-domain analysis and wavelet analysis, which could determine poses of human body (e.g. fall down, stand, sit, lie down, go upstairs, go downstairs, walk, etc.) by analyzing the readouts of a tri-axis accelerometer of the body pose detection module.

SUMMARY OF THE INVENTION

A first aspect of the present invention provides a multi-person pose recognition system, which includes a body pose detection module containing (1) a triaxial accelerometer for measuring an acceleration signal of a human body; (2) a Zigbee chip having at least a transmit/receive buffer, a voltage converter and an antenna, coupled with an interface of a microcontroller, and providing the data of on-line intensity and connection quality so as to ascertain connection status among nodes; and (3) a microcontroller having a plurality of A/D converters capable of converting an analog signal of the triaxial accelerometer into a digital signal, connected between the triaxial accelerometer and the Zigbee chip for controlling the sleep state of the triaxial accelerometer and selecting a measuring range of the triaxial accelerometer, and controlling the transmit/receive buffer of the Zigbee chip to read or write buffered data or respond with chip status information, in which the plural A/D converters of the microcontroller is sampled with 10-bit or 8-bit accuracy, and the development board of the Zigbee WSN is used to serve as a receiving end of the Zigbee WSN. Given the plural body pose detection modules and the development board of the Zigbee WSN, a Zigbee WSN enabling the plural body pose detection modules to mutually communicate could be constructed.

Preferably, the multi-person pose recognition system further includes a computer-monitoring end or a robot-monitoring end for examining user's pose and monitoring the state of each node in the entire network. The functions for examining user's pose and monitoring nodes are controlled by a multi-person monitoring software developed in the computer-monitoring end or the robot-monitoring end for simultaneously recording and compiling statistics of the received pose information so as to simultaneously monitor multi-person poses.

A second aspect of the present invention provides a method for estimating pose, which includes steps of abstracting a dynamic acceleration and a static acceleration from readouts of the triaxial accelerometer through a signal preprocessing step; checking if any abnormal signal caused by falling down exists in the dynamic acceleration; if no, analyzing the dynamic acceleration to determine whether the pose is static or dynamic; if the pose is determined to be static, determining the pose to be standing, sitting or lying according to the inclined angle of the human trunk; otherwise, if the pose is determined to be dynamic, detecting if there is a step movement through preprocessing steps for step movement detection and step movement determination; if detecting step movement in the step for step movement detection, applying wavelet transform to the acceleration signal to analyze wavelet coefficients of an energy distribution band while walking normally; calculating a characteristic parameter based on the wavelet coefficients to determine whether the step is a pose while walking, going upstairs or going downstairs; and if detecting no step movement, classifying the pose as an exercising state.

As such, by means of the multi-person pose recognition system together with the method for estimating pose (pose estimation algorithm), seven different poses of standing, sitting, walking, going upstairs, going downstairs and falling down could be successfully recognized. The analysis result is forwarded to a pose management program in a host computer (or a nursing robot) through the Zigbee WNS for compiling statistics and recording so as to achieve the effect of simultaneously monitoring multi-person poses.

To make the foregoing description and other objects, characteristics and advantages more definite and comprehensive, preferred embodiments in conjunction with the attached figures are depicted in details as follows.

DETAILED DESCRIPTION OF THE PREFERRED EMBODIMENT

Figure 1:
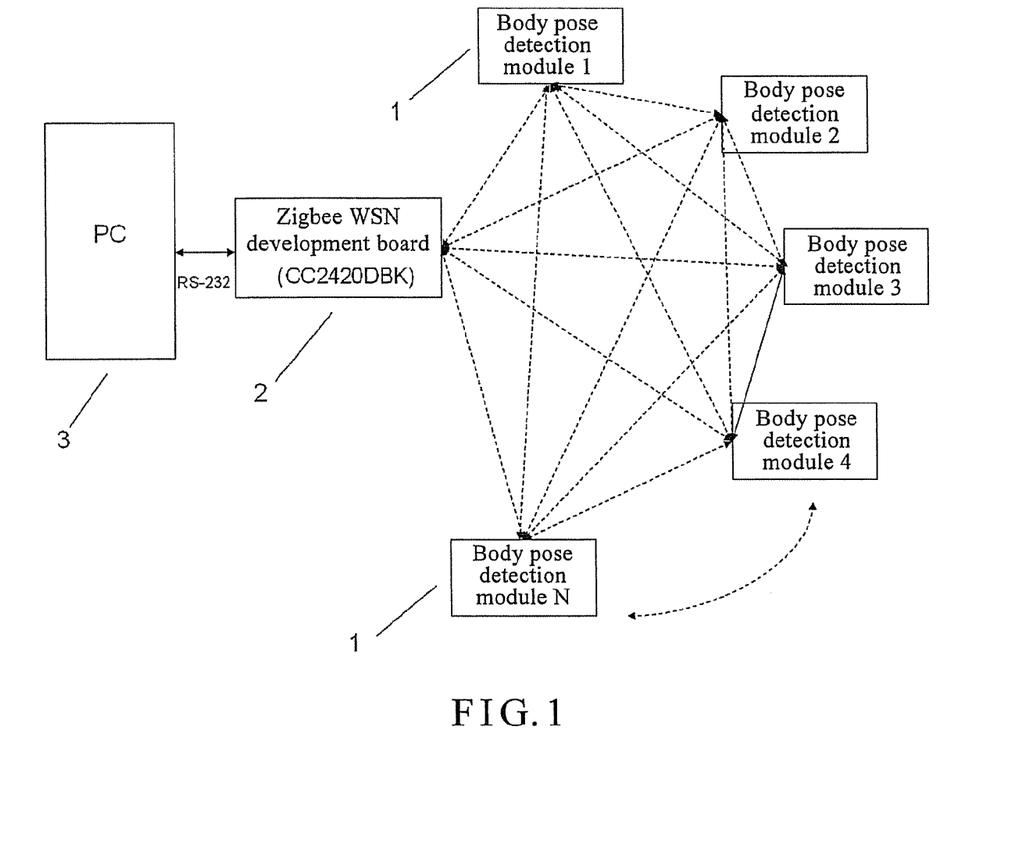
FIG. 1 is an architecture view showing a pose recognition system of the present invention.

Please refer to FIG. 1, which is an architecture view showing a pose recognition system of the present invention. The pose recognition system includes a plurality of body pose detection modules 1 capable of being mounted to a user's body, a Zigbee WSN development board (CC2420DBK) 2, and a host computer (or a robot onboard computer) 3. The present invention utilizes a plurality of body pose detection modules 1 and a CC2420DBK Zigbee WSN development board 2 to deploy a Zigbee WSN, in which the CC2420DBK 2 communicates with a host computer (or a robot onboard computer) 3 through a RS-232 port, and data in each node of the Zigbee WSN are integrated and monitored through the host computer (or the robot onboard computer) 3.

Figure 2:
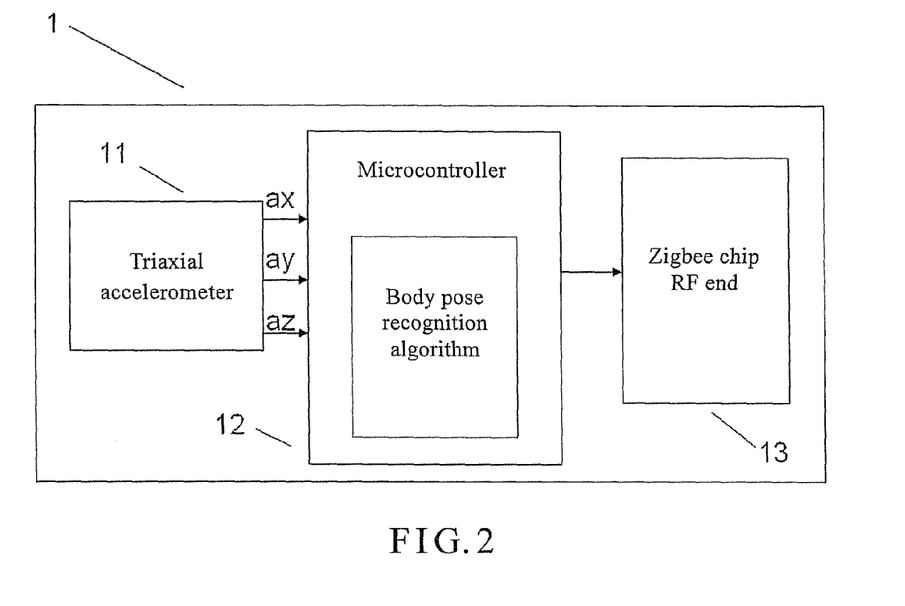
FIG. 2 is a block diagram showing an accelerometer, a microcontroller and a Zigbee chip (Chipcon CC2420)
Figure 3:
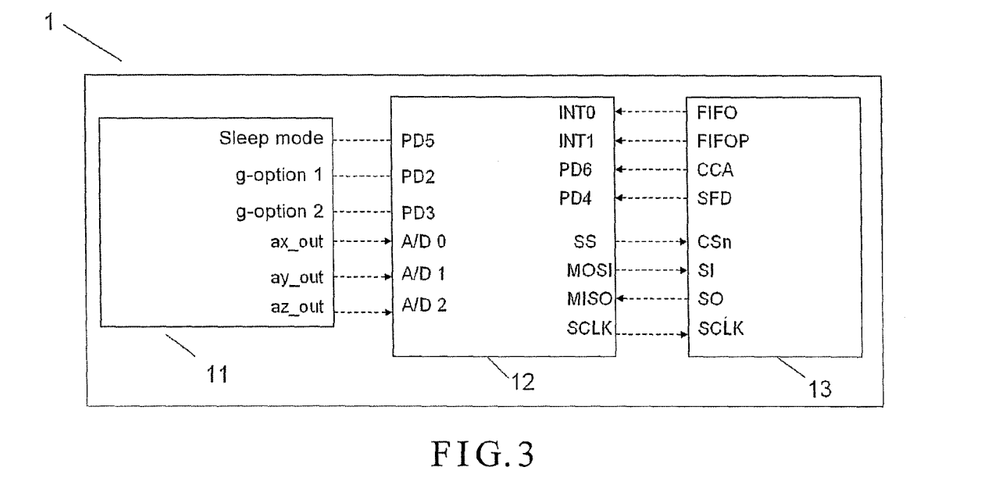
FIG. 3 is a schematic view showing the control interface of FIG. 2.

Further refer to FIG. 2 and FIG. 3, which a block diagram showing a triaxial accelerometer, a microcontroller and a Zigbee chip (Chipcon CC2420) and a schematic view showing the control interface of FIG. 2 respectively, in which the microcontroller is connected between the triaxial accelerometer and the Zigbee chip, pins PD2, PD3 and PD5 inside the microcontroller 12 are used to initialize the accelerometer, the PD5 controls if the triaxial accelerometer 11 is in the sleep mode, and the PD2 and PD3 control the g-option 1 pin and g-option 2 pin of the triaxial accelerometer 11 to select a detection range of the accelerometer 11.

As the output of the triaxial accelerometer is an analog signal, after high-frequency noises are filtered by a low-pass filter, the analog signal is entered to three A/D converters (A/D0, A/D1 and A/D3) of the microcontroller 12. Besides, the plural A/D converters are optional to sample with 10-bit or 8-bit accuracy. To facilitate explanation, the sampling with 8-bit accuracy is exemplified to explain the following embodiment.

Besides, right sides of FIG. 2 and FIG. 3 illustrate the interface connection between the microcontroller 12 and the Zigbee chip (CC2420) 13. The microcontroller 12 configures the state of the Zigbee chip 13 through the SPI interface (CSn, SI, SO, and SCLK) of the Zigbee chip 13, and controls buffered data read and written by the Zigbee chip 13 or responds with the status information of the Zigbee chip 13, in which the microcontroller 12 is a Master. Hence, its pin MOSI (Master Output Slave Input) is connected to the input SI of the Zigbee chip and its pin MISO (Master Input Slave Output) is connected to the output SO of the Zigbee chip 13. While the Zigbee chip 13 is operating, the pin CSn pin must be set to a low voltage, and the pin SCLK is the pin of the microcontroller 12 which provides clock signal to the Zigbee chip 13. The microcontroller 12 issues a command to the Zigbee chip via the SO pin and the SI pin to read from or write to a transmit/receive buffer in the Zigbee chip 13 and control the data read/write of the Zigbee chip 13. Besides, pins FIFO, FIFOP, SFD and CCA are used to inform the microcontroller of the status while reading or writing data.

Figure 4:
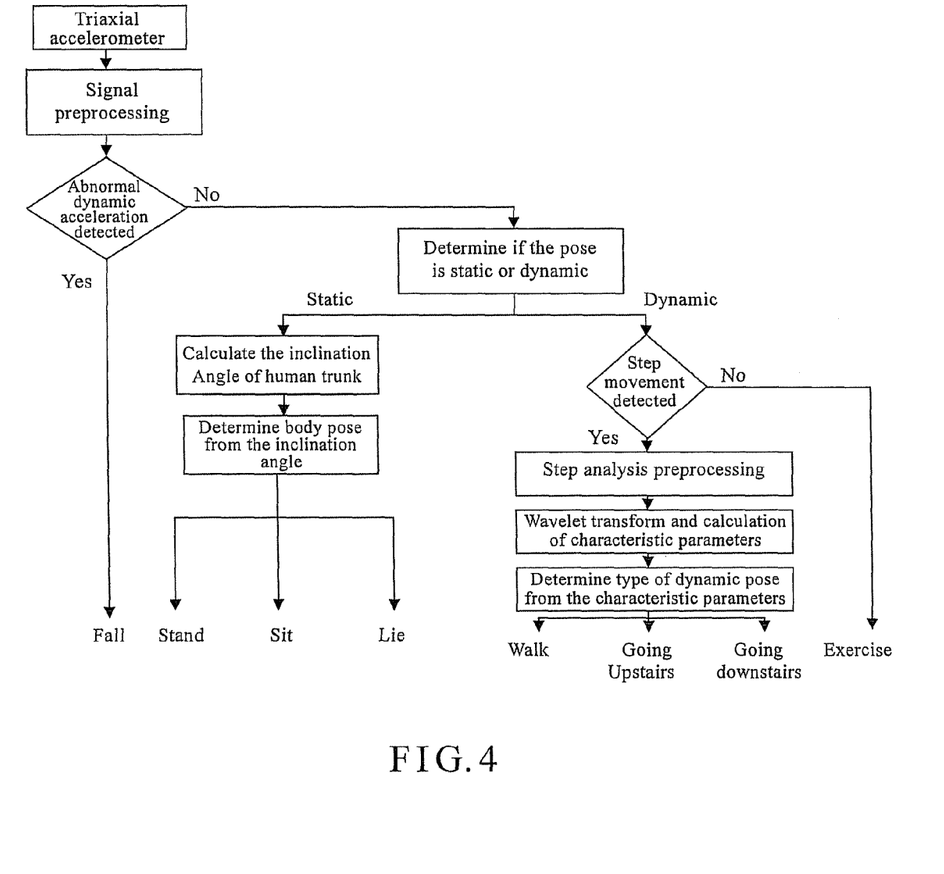
FIG. 4 is a flow chart showing the body pose detection algorithm of the present invention.

The present invention classifies recognized human body poses into three groups, namely unexpected situation, dynamic pose and static pose, in which the group of unexpected situation is set to contain a falling pose, the group of dynamic pose contains the poses of walking, going upstairs and going downstairs, and the group of static pose contains the poses of standing, sitting and lying. The inclination angle of a human trunk could be estimated by the component along each axis of the acceleration so that a relevant static pose could be estimated therefrom. A dynamic acceleration is resulted from an activity of human body and could be used to determine the dynamic poses of walking, going upstairs, going downstairs and falling. As shown in FIG. 4, which is a flow chart showing the body pose detection algorithm of the present invention, after performing a signal preprocessing of the readout of the triaxial accelerometer 11, the algorithm checks if there is any abnormal signal in the acceleration caused by falling down; if none, analyze the dynamic acceleration to determine if the human body is positioned in a dynamic pose or a static pose; If the human body is positioned in a static pose, determine the pose as one of standing, sitting and lying poses in accordance with the inclination angle of the human trunk; if the human body is positioned in a dynamic pose, determine if there is any step movement by steps for step movement detection and step analysis preprocessing; if detecting any step movement, apply wavelet transform to the acceleration signal to calculate a characteristic parameter, analyze wavelet coefficients of an energy distribution band while human being normally walks, and calculate the characteristic parameter defined by the present invention from those wavelet coefficients to further determine if the step movement pertains to a pose of walking, going upstairs or going downstairs; if detecting no step movement, classify the body pose as an exercising state.

In view of 99% or more of exercise frequencies of human body all smaller than 20 Hz, in accordance with the Shannon sampling theorem, the sampling frequency must be chosen to have a bandwidth greater than twice the bandwidth of a source signal. However, 5~10 folds of that of the source signal is usually required in actual application. Consequently, the sampling frequency adopted in the embodiment of the present invention is 128 Hz, and the overflow interrupt of the timer in a microcontroller is employed to control the sampling frequency.

To take both the response time and sufficient data amount of the system into account, data collected after every two seconds is selectively processed by a pose algorithm, that is, one body pose recognition for every 256 data. After fetching 256 data, first perform signal preprocessing to abstract a dynamic acceleration and a static acceleration. The present invention employs a wavelet transform method to calculate the static acceleration. As there are 256 data fetched, an eight-layer Haar wavelet transform could be performed accordingly. After the transformation, take one layer with the minimum frequency, which is indicative of the wavelet coefficient in a range of 0~0.25 Hz, and is indicative of the DC component of the two seconds after restoring from frequency domain to time domain. As for the dynamic acceleration, it is obtained by subtracting the static acceleration signal from the original acceleration signal.

Figure 5:
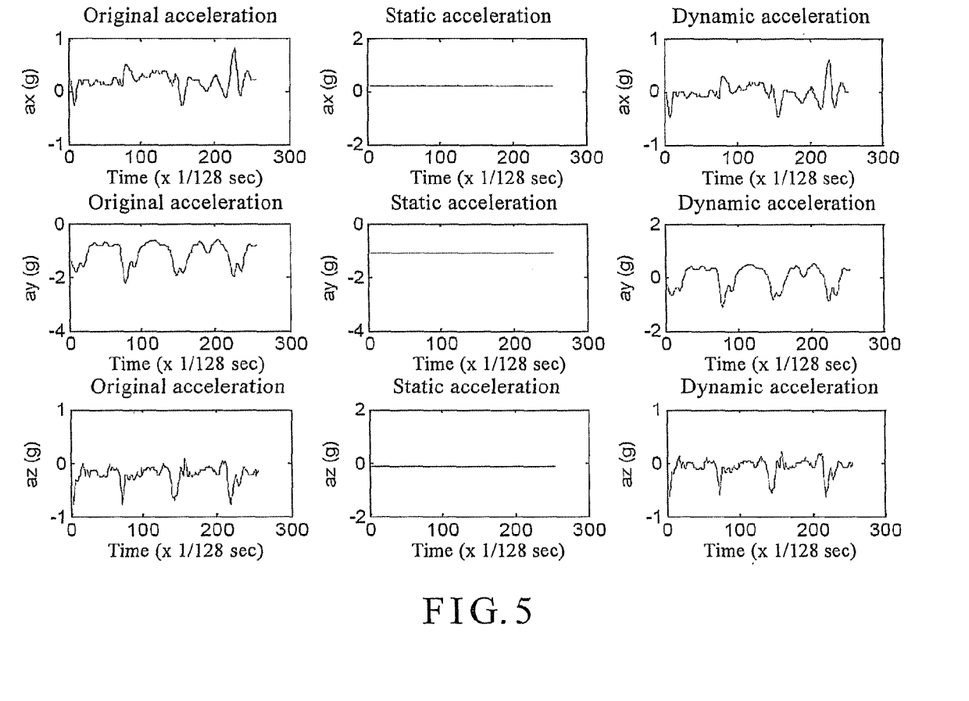
FIG. 5 is a curve chart showing the components of triaxial acceleration signal, static acceleration and dynamic acceleration.
Figure 6:
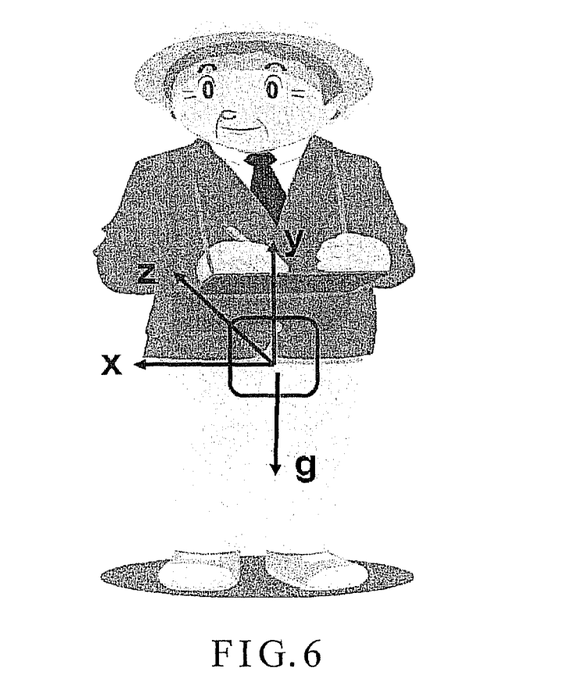
FIG. 6 is a relationship diagram showing the wearing condition of the body pose estimation module and acceleration of gravity.

Please refer to FIG. 5, which is a curve chart showing the components of triaxial acceleration signal, static acceleration and dynamic acceleration. The X-axis, Y-axis and Z-axis original acceleration signals of the triaxial accelerometer 11 are shown on the most left column of the curve chart and are the triaxial acceleration signals while walking. After applying wavelet transform to those original signals, keep a wavelet coefficient with the lowest frequency, which is recovered to obtain the static acceleration components on the second column of FIG. 5. Subtract those static acceleration signals from those original signals to obtain the dynamic acceleration components on the third column to the left in FIG. 5. Those static accelerations therein originate from the acceleration of gravity of the earth. Please refer to FIG. 6, which is a relationship diagram showing the wearing condition of the body pose estimation module and the acceleration of gravity. It can be seen that the human trunk is in an upright situation (e.g. walk or stand). The readout sensed along the y axis of the triaxial accelerometer 11 equals to −1 g (g is the acceleration of gravity of the earth) while the x axis and z axis of the triaxial accelerometer are not subjected to the influence of the acceleration of gravity. As a result, an ideal Y-axis static acceleration shall approach −1 g, and the static acceleration of the x axis and z axis shall approach 0 g. The static acceleration in FIG. 5 simply coincides with the induction of the present invention.

Figure 7:
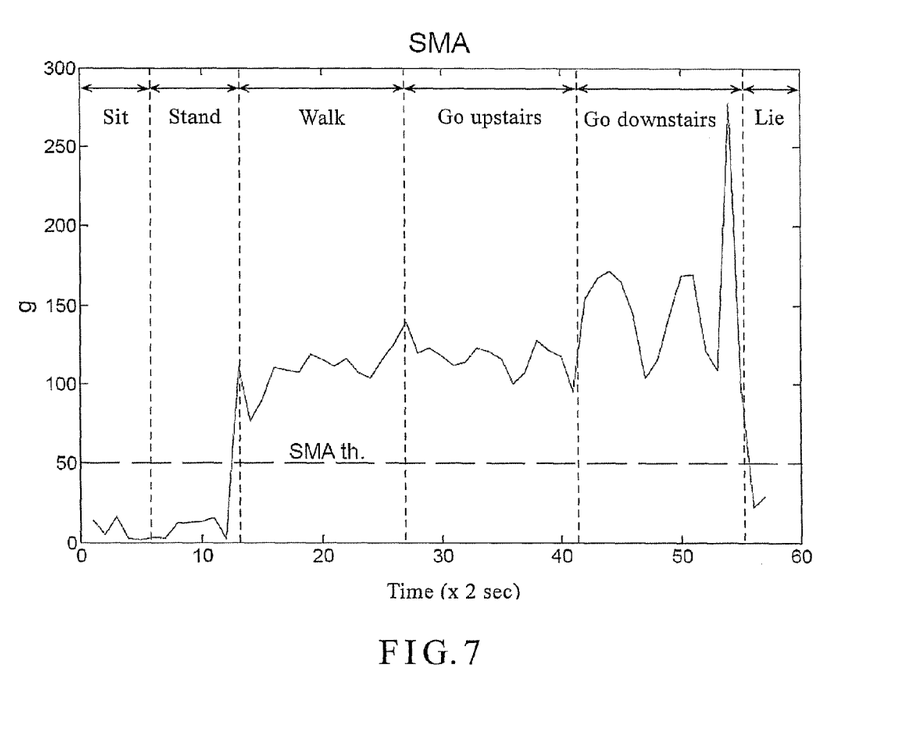
FIG. 7 is a distribution curve chart showing the signal magnitude area (SMA) of different poses.

Determination of Dynamic and Static Body Poses:

The present invention classifies body poses into two types, namely dynamic pose and static pose. Use the integral of the absolute values of the triaxial accelerations in Eqn (1) to obtain a signal magnitude area (SMA) of dynamic acceleration as follows, $$SMA = \sum_{n=0}^{256} (|a_{x\_dynamic}[n]| + |a_{y\_dynamic}[n]| + |a_{z\_dynamic}[n]|) \quad (1)$$

in which, the obtained SMA value is positively correlated with the energy generated from exercise of a human body. Hence, in case that such parameter is higher than certain threshold, it may be used to determine that the human body is in an exercising state momentarily, or the human body is in a static state. Please refer to FIG. 7, which is a distribution curve chart showing the SMA of different poses and shows the conditions of a human body in a static state or an exercising state. It can be seen that the SMA values for three static poses of standing, sitting and lying are far less than those for three dynamic poses of walking, going upstairs and going downstairs. While the SMA threshold is set to be 50 g, a body pose could be distinguished as a dynamic pose or a static pose.

Recognition of Falling Pose:

In view of acute variation to triaxial acceleration upon falling, the present invention employs the following eqn (2) to define the SMV and uses it to determine the falling situation:

$$SMV = a_{x\_dynamic}^2 + a_{y\_dynamic}^2 + a_{z\_dynamic}^2 \quad (2)$$

Figure 8:
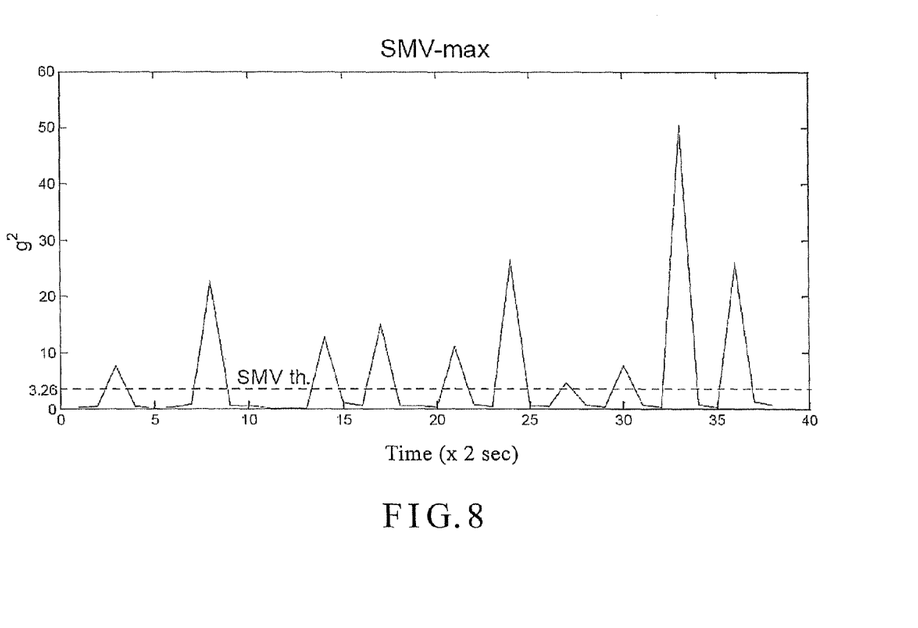
FIG. 8 is a curve chart showing the maximum value (SMV max) of the signal magnitude vectors (SMV) while a testee falls down ten times in a period of time.

When $a_{x\_dynamic}^2 + a_{y\_dynamic}^2 + a_{z\_dynamic}^2 > 3.24 \ g^2$, an extraordinary and acute acceleration to human body is determined to take place and is determined to be the case of falling down. The embodiment collects data every two seconds for a determination; hence, each of the three axes have 256 data. Calculate the largest SMV in the 256 sets of triaxial acceleration data to represent the SMV in the two seconds and define it as SMV_max. If the SMV_max is greater than 3.24, then determine that there is an occurrence of falling situation. Please refer to FIG. 8, which is a curve chart showing the SMV_max of the SMV while a testee falls down ten times in a period of time and showing the free movement of a user in a room. Ten local maximum values in FIG. 8 are the time spots when to fall. In addition, from FIG. 8 it could be found that SMV_max>3.24 upon falling and SMV_max upon falling is far greater than the SMV_max of any other pose.

Figure 9:
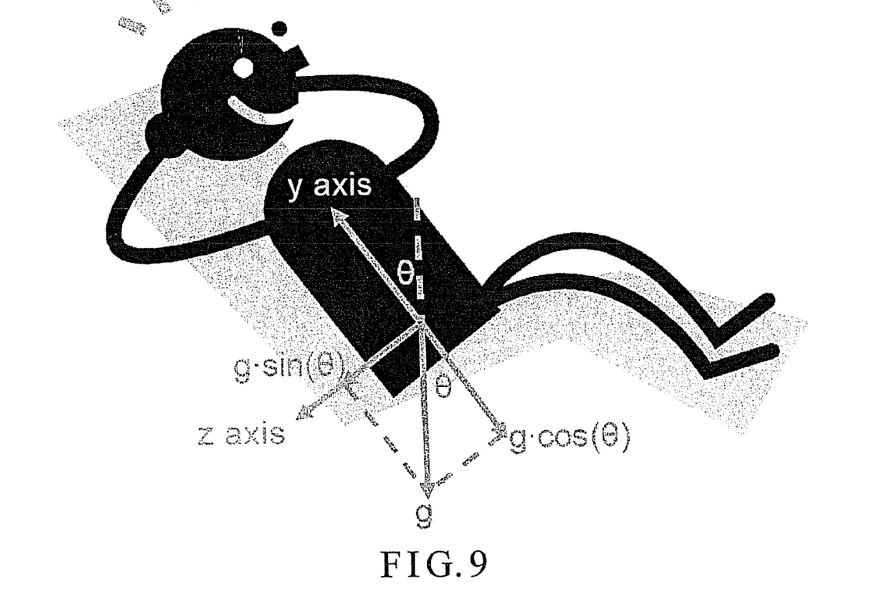
FIG. 9 is a schematic view showing the relationship between the inclination angle of human trunk and acceleration of gravity.

Recognition of Standing, Sitting and Lying Poses:

Standing, sitting and lying static poses could be determined by the inclination angle of a human trunk. In accordance with observation, if the inclined degree of the human trunk is greater than 60 degrees, the body is determined to be in a lying state; if the inclined degree of the human trunk is between 20 degrees to 60 degrees, the body is in a sitting state; if the inclined degree of the human trunk is between 0 degree to 20 degrees, the body is in a standing state. As the static acceleration arises from the component of the acceleration of gravity of the earth as shown in FIG. 9, the component of the acceleration of gravity along the trunk can be detected along the y sensing axis of the triaxial accelerometer 11 of the body detection module 1, which is parallel to the direction of the trunk. Therefore, the inclination angle of the human trunk could be determined by the static acceleration sensed along the y sensing axis. Because the acceleration value sensed along the y axis equals to the cosine component of the acceleration of gravity (i.e. $a_{y\_static} = g \cdot \cos(\theta)$) and $a_{y\_static\_th1} = g \cdot \cos(20°)$ and $a_{y\_static\_th2} = g \cdot \cos(60°)$ are two threshold values for determining the inclination angle of the trunk, $a_{y\_static}$ may comply with one of eqn (3)~(5):

$$g \cdot \cos(20°) < a_{y\_static} = g \cdot \cos(\theta) \leq g \cdot \cos(0°) \quad (3)$$

$$g \cdot \cos(60°) < a_{y\_static} = g \cdot \cos(\theta) \leq g \cdot \cos(20°) \quad (4)$$

$$a_{y\_static} = g \cdot \cos(\theta) \leq g \cdot \cos(60°) \quad (5)$$

As the cosine function is a decreasing function in a range of $\theta < 90°$, if eqn (3) holds true, it means $0° < \theta < 20°$ or the pose is determined to be a standing pose; if eqn (4) holds true, it means $20° < \theta < 60°$ or the pose is determined to be a sitting pose; if eqn (5) holds true, it means $\theta > 60°$ or the pose is determined to be a lying pose.

Recognition of Poses of Walking, Going Upstairs and Going Downstairs:

The present invention recognizes the poses of walking, going upstairs and going downstairs through the wavelet coefficients. However, the wavelet transform requires longer data for analysis so as to acquire substantial result. If adding more data sampling to increase data amount, it will make the system response time longer. The embodiment here attempts not to increase the recognition time but have a sufficient data amount which is enough to stand out the features after wavelet transform.

Figure 10:
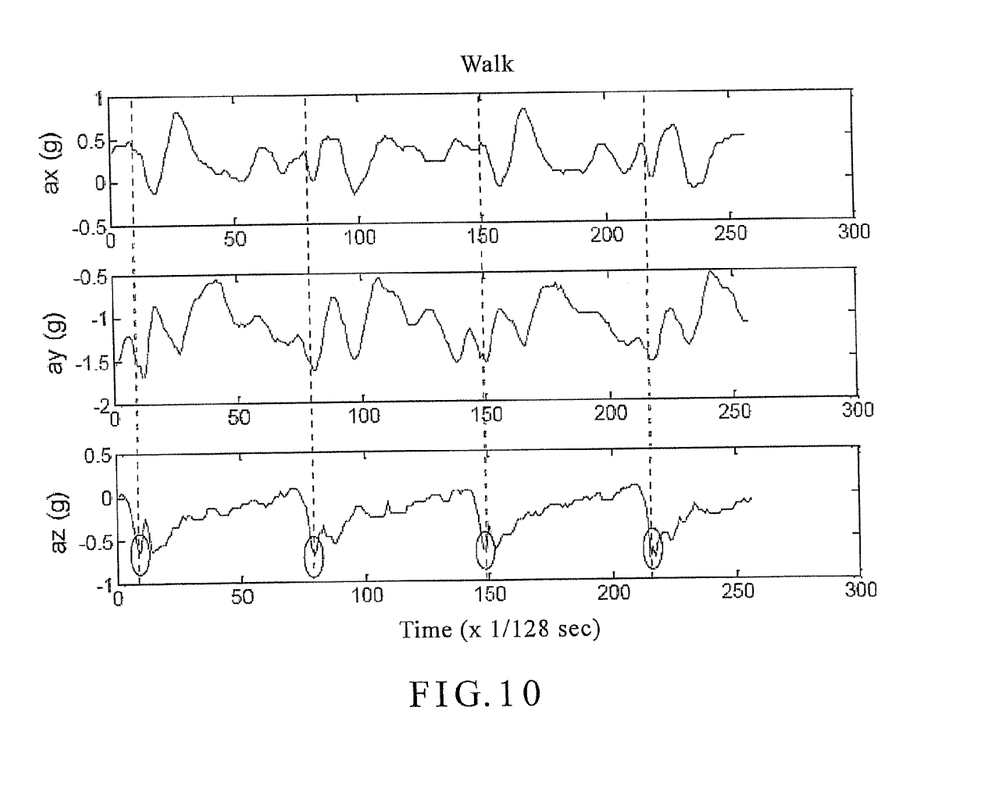
FIG. 10 is a waveform chart showing triaxial acceleration while walking.
Figure 11:
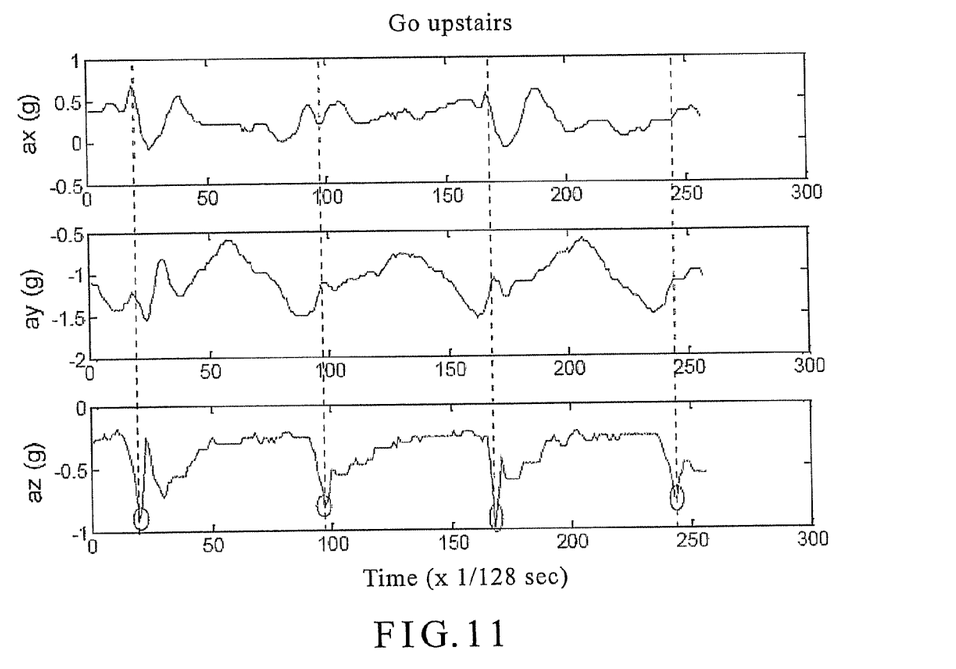
FIG. 11 is a waveform chart showing triaxial acceleration while going upstairs.
Figure 12:
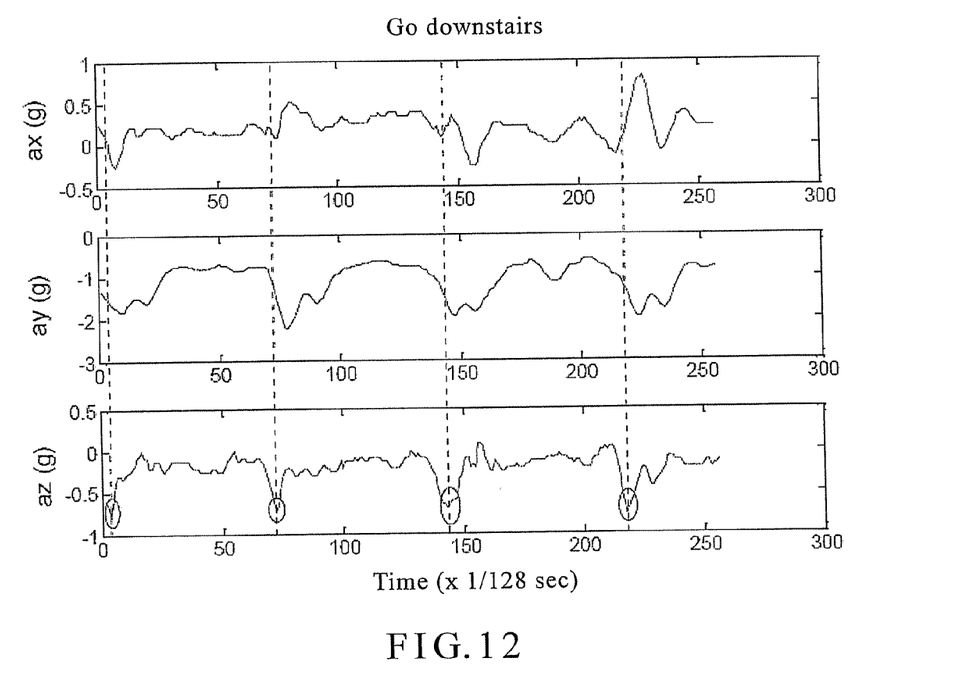
FIG. 12 is a waveform chart showing triaxial acceleration while going downstairs.

Please refer to FIG. 10 to FIG. 12, which are the waveform charts showing Y-axis and Z-axis accelerations (X axis involves the acceleration of the left-to-right sway and thus has little reference value) in association with three steps of walking, going upstairs and going downstairs. The waveforms for the accelerations of the three poses in those figures roughly exhibit a cyclic state. Hence, if the cycle unit of the poses can be located, then the cycle unit could be cyclized repeatedly, meaning that any random signal length could be obtained in favor of the wavelet transform.

Moreover, it can be seen from FIG. 10 to 12 that the Z-axis accelerations of the three steps (walk, go upstairs and go downstairs) all have an apparent local minimum upon starting each step. This local minimum could be taken as a beginning characteristic of steps. The signals between two local minimums are the acceleration signals generated while a testee walks every step. Since left and right feet grow in a somewhat different fashion, the forces exerted by left and right feet may be inconsistent. Therefore, the embodiment fetches two consecutive steps, i.e. one step for each of left and right feet, and uses the two consecutive steps as one cycle. The accelerations are cyclized to have 512 data for the calculation of the wavelet transform.

Figure 13:
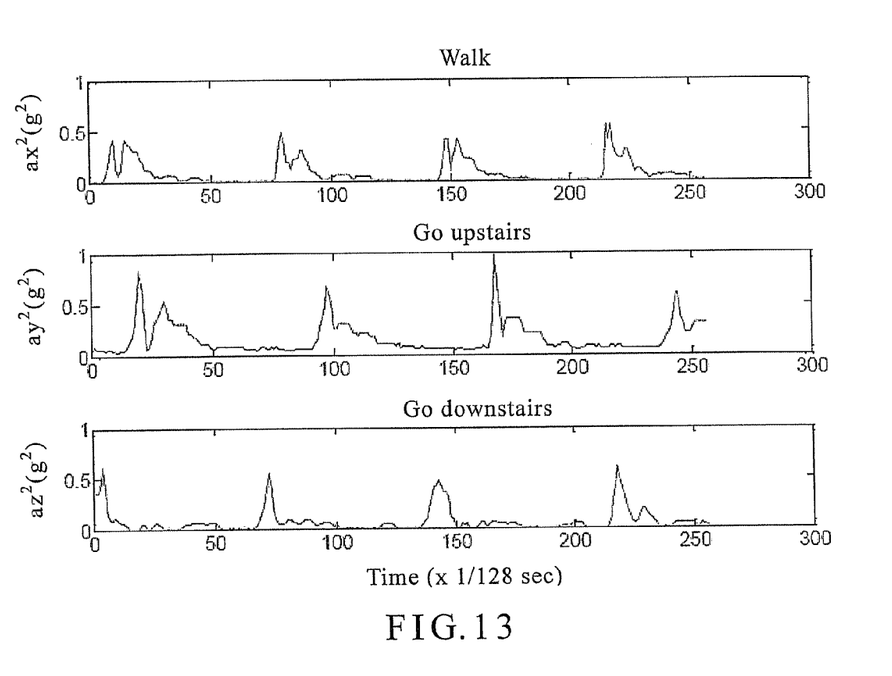
FIG. 13 is a waveform chart showing the square of Z-axis acceleration while walking, and going upstairs and downstairs.
Figure 14:
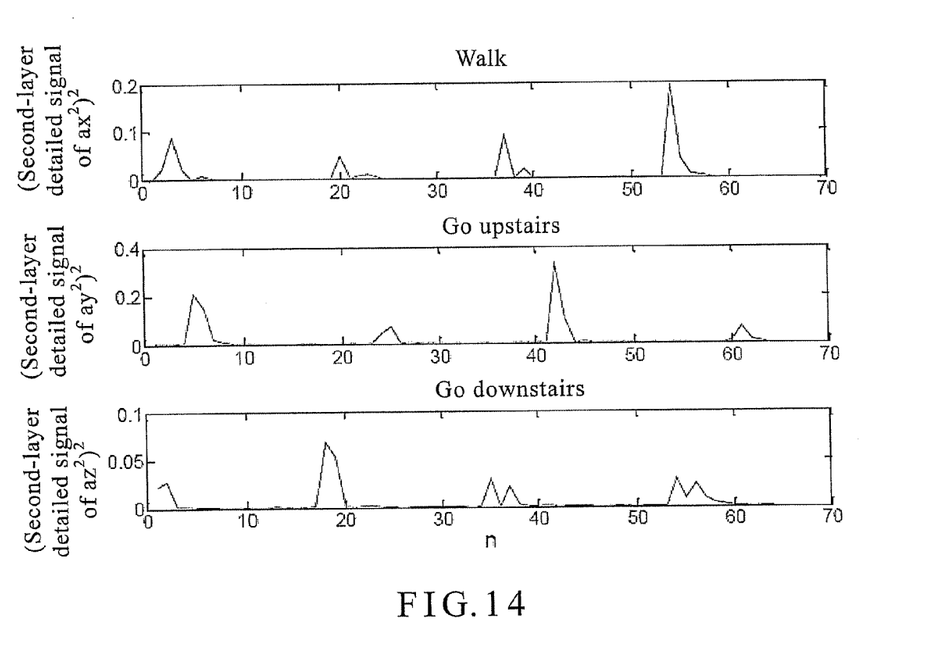
FIG. 14 is a waveform chart showing the local maximum value located by using the second-layer wavelet parameter.
Figure 15:
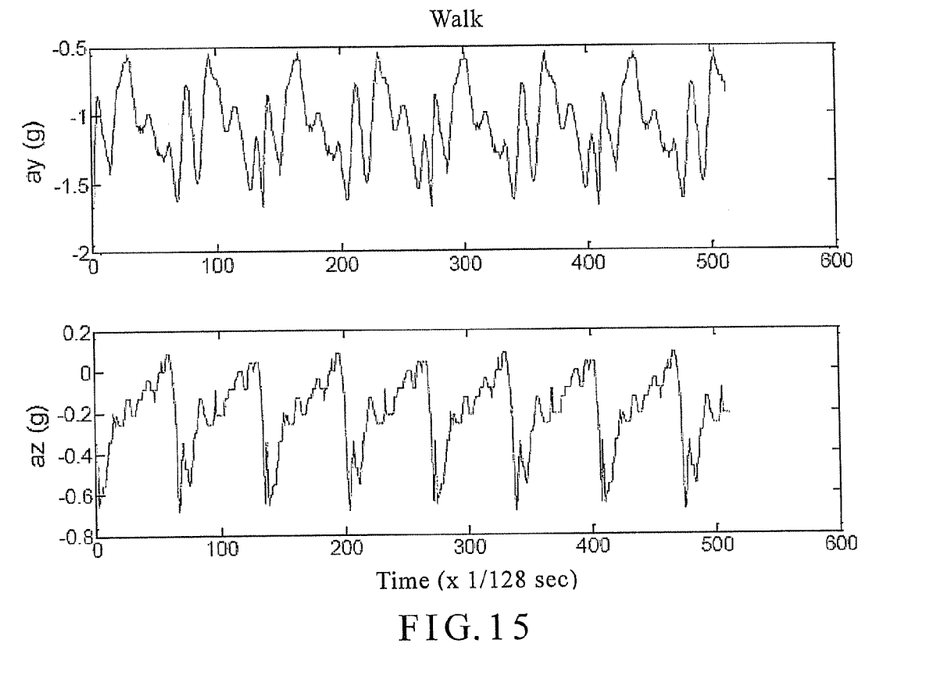
FIG. 15 is a waveform chart showing cyclization up to 512 points while waking.
Figure 16:
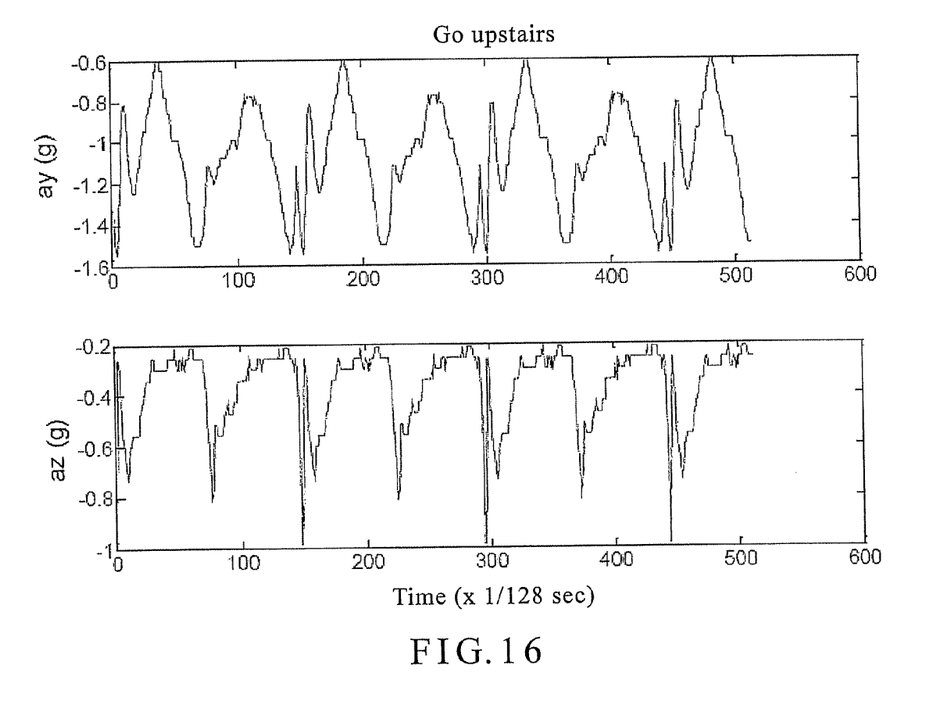
FIG. 16 is a waveform chart showing cyclization up to 512 points while going upstairs.
Figure 17:
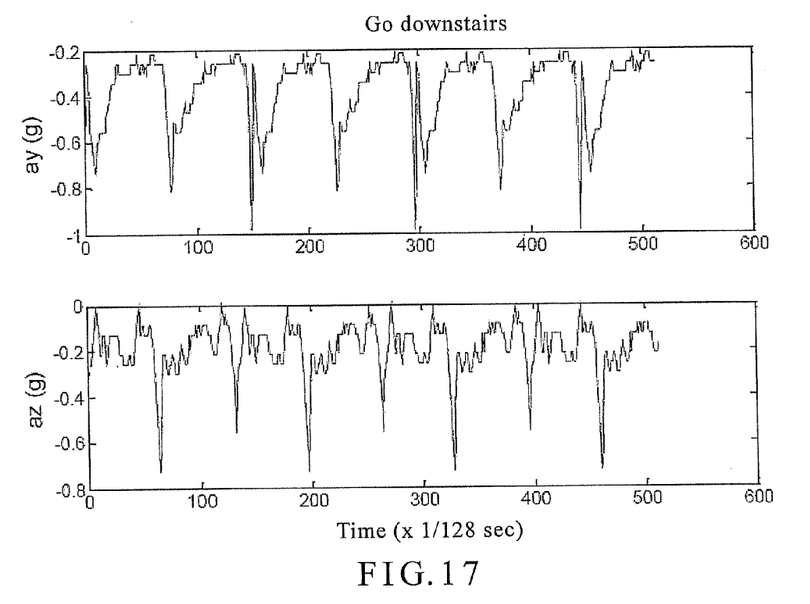
FIG. 17 is a waveform chart showing cyclization up to 512 points while going downstairs.

To rapidly locate the position of the local maximum, first apply a square operation to the Z-axis acceleration within two seconds to make the variation of the Z-axis acceleration more evident, and the result is as shown in FIG. 13, which is a waveform chart showing the square of Z-axis acceleration while walking, and going upstairs and downstairs. The local maximum is the position where a step movement starts. Next apply two-layer wavelet transform to the $a_z^2$ signal in the first step. As the position where step movement occurs contains high-frequency ingredient, the position where the local maximum occurs could be located by the wavelet coefficients after the wavelet transform as shown in FIG. 14 which is a waveform chart showing the local maximum value located by using the second-layer wavelet parameter. In view of the wavelet transform featuring time-frequency transition characteristics, the approximate position where the local maximum occurs in time domain could be estimated by the position where the local maximum of wavelet coefficients occurs, and thus the position where the step movement occurs could be rapidly found. The embodiment attempts to analyze the time-domain signals between two steps (one step for each of left and right feet). Hence, the time-domain signals between the first and the third local maximums are taken as the target for step analysis. Subsequently take the Y-axis and Z-axis accelerations between the time spots where the first local maximum and the third local maximum of the Z axis occur. Cyclize the Y-axis acceleration data ay and Z-axis acceleration data az up to 512 points as shown in FIG. 15 to FIG. 17 to complete the preprocessing procedures of step movement determination.

Apply nine-layer Haar wavelet transform to the cyclized step vectors of the 512 points to abstract the signal component of each frequency band. As the frequency band pertinent to human walking is distributed over 1~16 Hz, the present invention treats the wavelet coefficients distributed over the band of 1~16 Hz as the energy of the three types of exercising states. The phenomenon observed by experiment is that frequency for the pose variation of going upstairs is in a range lower than 1 Hz due to more pose variation. Hence, the energy in the z-axis direction (front side of human body) upon going upstairs is the least and its proportion out of the total energy az is also the least. The present invention employs the observed phenomenon to define a characteristic parameter called RTF. The pose of going upstairs is distinguished by using the RTF when it exceeds certain threshold value, in which the RTF equation is expressed by Eqn (5) as follows:

$$RTF = \frac{\|a_z\|_2^2}{\sum_{j=3}^{6} d_{zj}} \quad (6)$$

where $a_z$ is the Z-axis acceleration, $d_z$ is the Z-axis wavelet decomposition coefficient.

Regarding the determination of the poses of going downstairs and walking, as the energy in the Y axis of the triaxial accelerometer is the highest (vertical direction) and the force exerted in the Z axis is far below that by walking, the present invention defines another characteristic parameter RVF, which is expressed by Eqn (7) as follows:

$$RVF = \frac{\sum_{j=3}^{6} d_{yj}}{\sum_{j=3}^{6} d_{zj}} \quad (7)$$

where $d_y$ is the Y-axis wavelet decomposition coefficient, and $d_z$ is the Z-axis wavelet decomposition coefficient.

Figure 18:
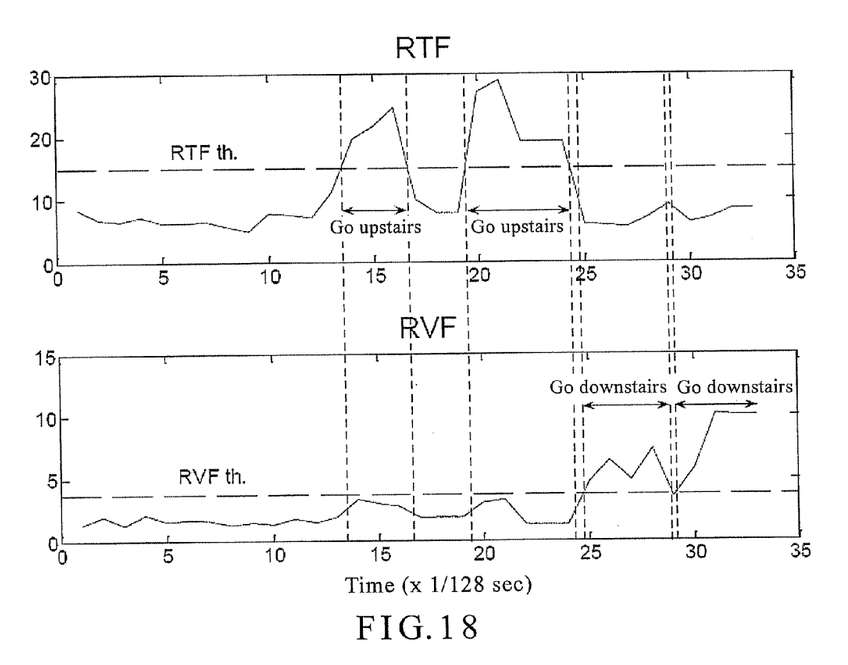
FIG. 18 is a waveform chart determined by RTF and RVF while waking and going upstairs and downstairs.

Given the RVF, the poses of going downstairs and walking could be distinguished. If the RVF is greater than certain threshold, the pose is determined to be walking downstairs. The three poses of walking, going upstairs and going downstairs could be determined by combining the two parameters, RTF and RVF. Please refer to FIG. 18, which is a waveform chart showing the variation of RTF and RVF recorded while waking and going upstairs to $7^{th}$ floor and going downstairs to $6^{th}$ floor. Significant value change of RTF is found in FIG. 18 while going upstairs and significant value change of RVF is found in FIG. 18 while going downstairs. Therefore, the pose is determined to be going upstairs, going downstairs or walking when RTF>15 or RVF>4 or otherwise, so that the poses of walking, going upstairs and going downstairs could be determined.

While the invention has been described in terms of what is presently considered to be the most practical and preferred embodiments, it is to be understood that the invention needs not be limited to the disclosed embodiments. On the contrary, it is intended to cover various modifications and similar arrangements included within the spirit and scope of the appended claims, which are to be accorded with the broadest interpretation so as to encompass all such modifications and similar structures. For instance, the system of the present invention may employ star, ring or other topology to construct a Zigbee WSN. As long as the added count of persons to be monitored does not exceed the upper limit of the multi-person pose management software and the transmission range won't go beyond the coverage of the Zigbee WSN, persons to be monitored can be added to the Zigbee WSN at any time. The present invention could be integrated with a wireless network and a nursing robot having 3G functions. Through a face tracking feature of the robot and video conferencing via the wireless network, the present invention could immediately detect falling situation of the aged and inform the family by using a mobile phone to send an emergency short message. The robot could also actively move beside the aged, transmit real-time images to a remote PDA so as to let the family or doctor swiftly know the condition of the aged and allow the injured aged to be rescued as soon as possible. Besides, the body pose detection module of the present invention could be connected with various sensors (e.g. body infrared sensor capable of detecting if a human body passes by, or a microphone detector and a motion detector capable of detecting if a glass is smashed), which are deployed in the surrounding, through the I/O pins thereof. When the sensors detect any abnormal condition, the nursing robot will go to the scene to look into the situation and transmit the image to the family, making the nursing robot provide not only home care function but also security services. As such, the protection range of the present invention depends on those defined in the subsequent claims.

What is claimed is:

1. A method for estimating a body pose in a body pose detection module provided with a triaxial accelerometer within a wireless sensor network of a plurality of body pose detection modules arranged to detect and simultaneously monitor body poses of multiple users, the method comprising steps of:

performing signal pre-processing of a triaxial acceleration signal readout from the triaxial accelerometer at the body pose detection module attached to a user body so as to abstract a dynamic acceleration and a static acceleration of the triaxial acceleration signal;

determining whether the dynamic acceleration of the triaxial acceleration signal is abnormal indicating that a body pose is a falling pose; and when the dynamic acceleration of the triaxial acceleration signal is not abnormal, analyzing the dynamic acceleration of the triaxial acceleration signal to determine whether a body pose is one of a static pose and a dynamic pose, wherein the signal preprocessing is performed by:
sampling from the triaxial acceleration signal readout from the triaxial accelerometer, each of sensing axes collecting 256 acceleration data, with a sampling frequency of 128 Hz and performing the signal preprocessing once at every two seconds;
subjecting acceleration data of the sensing axes of the triaxial acceleration signal to an eight-layer Haar wavelet transform;
maintaining a wavelet transform coefficient of the eight-layer Haar wavelet transform with a lowest frequency, while omitting other wavelet transform coefficients;
converting the wavelet transform coefficient of the lowest frequency into a time domain to represent the static acceleration of the triaxial acceleration signal; and
subtracting the static acceleration from the triaxial acceleration signal to obtain the dynamic acceleration of the triaxial acceleration signal.

2. The method as claimed in claim 1, further comprising a step of determining the body pose as a standing, sitting or lying pose in accordance with an inclination angle of a user trunk, if the body pose is determined as a static pose.

3. The method as claimed in claim 2, wherein the inclination angle of the body trunk is determined by the static acceleration sensed along a Y sensing axis of the triaxial accelerometer, and which one of the standing, sitting or lying pose the body pose pertains to is determined by steps of:
determining the body pose as a standing pose if g·cos(20°)< g·cos(θ)≦g·cos(0°);
determining the body pose as a sitting pose if g·cos(60°)< g·cos(θ)≦g·cos(20°); and
determining the body pose as a lying pose if g·cos(θ)≦ g·cos(60°);
where g is an acceleration of gravity of the earth, θ is an included angle between the acceleration of gravity of the earth, and the Y sensing axis of the axial accelerometer, g·cos(θ) represents the static acceleration sensed along the Y sensing axis and is a cosine component of the acceleration of gravity of the earth.

4. The method as claimed in claim 1, wherein the static acceleration is a component of the acceleration of gravity of the earth.

5. The method as claimed in claim 1, further comprising a step of detecting if a step movement exists through signal preprocessing for a step movement detection and a step movement determination, if the body pose is determined as a dynamic pose.

6. The method as claimed in claim 5, wherein the signal preprocessing for step movement detection and step movement determination further comprises:
using a local minimum in a Z-axis acceleration signal of the body pose to be determined as an initial characteristic value of the step movement;
fetching two consecutive steps as one cycle and providing cyclized acceleration data up to a preset amount for the calculation of the wavelet transform;
performing a two-layer wavelet transform to the square of the Z-axis acceleration signal; and
locating a position of a local maximum by virtue of wavelet coefficients after the wavelet transform and then estimating an approximate position where the local maximum in the time domain occurs.

7. The method as claimed in claim 5, further comprising steps of:
if the step movement is detected,
applying a wavelet transform to the triaxial acceleration signal;
analyzing wavelet coefficients of an energy distribution band while the user body is walking normally;
calculating characteristic parameters in accordance with the wavelet coefficients; and
determining, based on the step movement, if the body pose is a walking pose, or pose of going upstairs or downstairs;
otherwise
classifying the step movement as an exercising state.

8. The method as claimed in claim 7, wherein the characteristic parameters comprise:
an RTF for determining if the step movement is a body pose while going upstairs, when a RTF value exceeds a preset threshold; and
an RVF for determining if the step movement is a body pose while going downstairs, when a RVF value exceeds a preset threshold.

9. The method as claimed in claim 8, wherein the RTF is expressed by the equation as follows:

$$RTF = \frac{\|a_z\|_2^2}{\sum_{j=3}^{6} d_{zj}}$$

where $a_z$ is a Z-axis acceleration, and $d_z$ is a Z-axis wavelet decomposition coefficient.

10. The method as claimed in claim 8, wherein the RVF is expressed by the equation as follows:

$$RVF = \frac{\sum_{j=3}^{6} d_{yj}}{\sum_{j=3}^{6} d_{zj}}$$

where $d_y$ is a Y-axis wavelet decomposition coefficient, and $d_z$ is a Z-axis wavelet decomposition coefficient.

* * * * *